(12) United States Patent
Brooks

(10) Patent No.: US 7,811,586 B2
(45) Date of Patent: Oct. 12, 2010

(54) METHODS FOR ALLEVIATING TESTICULAR PAIN

(75) Inventor: Gregory F. Brooks, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 234 days.

(21) Appl. No.: 11/417,335

(22) Filed: May 2, 2006

(65) Prior Publication Data

US 2007/0259000 A1 Nov. 8, 2007

(51) Int. Cl.
- A61K 39/38 (2006.01)
- A61K 39/02 (2006.01)
- A61K 39/08 (2006.01)
- A61K 38/00 (2006.01)

(52) U.S. Cl. .............. 424/247.1; 424/236.1; 424/239.1; 530/300; 530/324

(58) Field of Classification Search ........................ None
See application file for complete search history.

(56) References Cited

U.S. PATENT DOCUMENTS

| | | | |
|---|---|---|---|
| 5,427,291 A | 6/1995 | Smith | 224/250 |
| 5,670,484 A | 9/1997 | Binder | 514/14 |
| 5,674,205 A | 10/1997 | Pasricha et al. | 604/232 |
| 5,714,468 A | 2/1998 | Binder | 514/14 |
| 5,766,605 A | 6/1998 | Sanders et al. | 424/239.1 |
| 5,989,545 A | 11/1999 | Foster et al. | 424/183.1 |
| 6,063,768 A | 5/2000 | First | 514/14 |
| 6,113,915 A | 9/2000 | Aoki et al. | 424/236.1 |
| 6,139,845 A | 10/2000 | Donovan | 424/236.1 |
| 6,143,306 A | 11/2000 | Donovan | 424/236.1 |
| 6,235,289 B1 | 5/2001 | Aoki et al. | 424/236.1 |
| 6,265,379 B1 | 7/2001 | Donovan | 514/14 |
| 6,299,893 B1 | 10/2001 | Schwartz et al. | 424/422 |
| 6,306,403 B1 | 10/2001 | Donovan | 424/239.1 |
| 6,306,423 B1 | 10/2001 | Donovan et al. | 424/423 |
| 6,312,708 B1 | 11/2001 | Donovan | 424/423 |
| 6,328,977 B1 | 12/2001 | Donovan | 424/239.1 |
| 6,333,037 B1 | 12/2001 | Aoki et al. | 424/236.1 |
| 6,358,513 B1 | 3/2002 | Voet et al. | 424/239.1 |
| 6,365,164 B1 | 4/2002 | Schmidt | 424/239.1 |
| 6,372,226 B2 | 4/2002 | Aoki et al. | 424/236.1 |
| 6,395,277 B1 | 5/2002 | Graham | 424/184.1 |
| 6,423,319 B1 | 7/2002 | Brooks et al. | 424/239.1 |
| 6,458,365 B1 | 10/2002 | Aoki et al. | 424/239.1 |
| 6,464,986 B1 | 10/2002 | Aoki et al. | 424/239.1 |
| 6,776,991 B2 | 8/2004 | Naumann | 424/239.1 |
| 6,869,610 B2 | 3/2005 | Aoki et al. | 424/239.1 |
| 6,887,476 B2 | 5/2005 | Aoki et al. | 424/184.1 |
| 2004/0126380 A1 | 7/2004 | Schmidt | |
| 2004/0180065 A1 | 9/2004 | Schmidt | |
| 2005/0049175 A1 | 3/2005 | Schmidt | |
| 2005/0112147 A1 | 5/2005 | Schmidt | 424/239.1 |

FOREIGN PATENT DOCUMENTS

| | | |
|---|---|---|
| EP | 0 605 501 B1 | 4/1999 |
| WO | WO 95/17904 | 7/1995 |

OTHER PUBLICATIONS

Granitsiotis (European Urology, 45 (2004) 430-436).*
Cakmak et al (Urol. Res. (2003), 31:352-354).*
Forte et al (Chir Ital. Jan.-Feb. 2003;55(1):145-7)(Abstract only).*
Mense (J Neurol (2004) 251[Suppl 1]:1/1-1/7).*
Freund et al, Journal of Pain, vol. 4, No. 3 (Apr. 2003), pp. 159-165.*
Cremaster muscle, Dictionary.com, http://dicitionary.reference.com.*
Orchitis, Dictionary.com, http://dicitionary.reference.com.*
Spermatic cord, Dictionary.com, http://dicitionary.reference.com.*
Fisher et al (Human Reproduction, 2003, vol. 18, No. 7, p. 1383-1394).*
Bigalke H., et al., *Botulinum A Clostridial toxin Inhibits Non-Cholinergic Synaptic Transmission in Mouse Spinal Cord Neurons in Culture*, Brain Research 360;318-324:1985.
Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.
Binz T. et al., *The Complete Sequence of Botulinum Clostridial toxin Type A and Comparison with Other Clostridial toxins*, J Biological Chemistry 265(16);9153-9158:1990.
Boyd R.S. et al., The effect of botulinum Clostridial toxin-B on insulin release from a ∃-cell line, *Mov Disord*, 10(3):376:1995.
Boyd R.S. et al., The insulin secreting ∃-cell line, HIT-15, contains SNAP-25 which is a target for botulinum Clostridial toxin-A, *Mov Disord*, 10(3):376:1995.

(Continued)

Primary Examiner—Vanessa L. Ford
(74) Attorney, Agent, or Firm—Kenton Abel; Claude Nassif; Debra Condino

(57) ABSTRACT

Method for alleviating testicular pain in a patient in need thereof. The method can comprise the step of locally administering a neurotoxin (e.g., a botulinum toxin) to at least one anatomical site selected from the group consisting of a testicle and a tissue associated with the testicle of the patient.

26 Claims, 4 Drawing Sheets

OTHER PUBLICATIONS

Cakmak et al. (2003) Urol Res 31:352-354.

Dykstra, D.D., et al, *Treatment of detrusor-sphincter dyssynergia with botulinum A toxin: A double-blind study*, Arch Phys Med Rehabil Jan. 1990;71:24-6.

Gonelle-Gispert, C., et al., *SNAP-25a and —25b isoforms are both expressed in insulin-secreting cells and can function in insulin secretion*, Biochem J. 1;339 (pt 1):159-65:1999.

Granitsiotis et al., European Urology (2004) 45:430-436, at p. 431.

Habermann E., et al., *Tetanus Toxin and Botulinum A and C Clostridial toxins Inhibit Noradrenaline Release From Cultured Mouse Brain*, J Neurochem 51(2);522-527:1988.

Habermann E., *Inhibition by Tetanus and Botulinum A Toxin of the release of [$^3$H]Noradrenaline and [$^3$H]GABA From Rat Brain Homogenate*, Experientia 44;224-226:1988.

Habermann, $^{125}$I-labelled Clostridial toxin from clostridium botulinum A: preparation, binding to synaptosomes and ascent to the spinal cord, Nauny-Schmiedeberg's Arch. Pharmacol. 1974; 281, 47-56.

*Harrison's Principles of Internal Medicine* (1998), edited by Anthony Fauci et al., 14$^{th}$ edition, published by McGraw Hill.

Coffield, et al., Eds. Jankovic J. et al., *Therapy With Botulinum Toxin*, Marcel Dekker, Inc., (1994), p. 5.

Kohl A., et al., *Comparison of the effect of botulinum toxin A (BOTOX (R)) with the highly-purified Clostridial toxin (NT 201) in the extensor digitorum brevis muscle test*, Mov Disord 2000;15(Suppl 3):165.

Marjama-Lyons, J., et al., *Tremor-Predominant Parkinson's Disease*, Drugs & Aging 16(4);273-278:2000.

Moyer E et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.

Naumann M., et al., *Botulinum toxin type A in the treatment of focal, axillary and palmar hyperhidrosis and other hyperhidrotic conditions*, European J. Neurology 6 (Supp 4): S111-S115:1999.

Pearce, L.B., *Pharmacologic Characterization of Botulinum Toxin For Basic Science and Medicine*, Toxicon 35(9);1373-1412 at 1393.

Ragona, R.M., et al., *Management of parotid sialocele with botulinum toxin*, The Laryngoscope 109:1344-1346:1999.

Rohrbach S., et al., *Botulinum toxin type A induces apoptosis in nasal glands of guinea pigs*, Ann Otol Rhinol Laryngol Nov. 2001;110(11):1045-50.

Rohrbach S., et al., *Minimally invasive application of botulinum toxin type A in nasal hypersecretion*, J Oto-Rhino-Laryngol Nov.-Dec. 2001;63(6):382-4.

Sanchez-Prieto, J., et al., *Botulinum Toxin A Blocks Glutamate Exocytosis From Guinea Pig Cerebral Cortical Synaptosomes*, Eur J. Biochem 165;675-681:1987.

Schantz E.J., et al *Preparation and characterization of botulinum toxin type A for human treatment* (in particular pp. 44-45), being chapter 3 of Jankovic, J., et al, *Therapy with Botulinum Toxin*, Marcel Dekker, Inc (1994).

Schantz, E.J., et al, *Properties and use of Botulinum toxin and Other Microbial Clostridial toxins in Medicine*, Microbiol Rev. 56;80-99:1992.

Singh, *Critical Aspects of Bacterial Protein Toxins*, pp. 63-84 (chapter 4) of Natural Toxins II, edited by B.R. Singh et al., Plenum Press, New York (1996).

Sloop, R., et al., Neurology, 1998 (48), pp. 249-253.

Weigand et al, $^{125}$I-labelled botulinum A Clostridial toxin:pharmacokinetics in cats after intramuscular injection, Nauny-Schmiedeberg's Arch. Pharmacol. 1976; 292, 161-165.

Westhoff et al. (2002) Naunyn Schmiedebergs Arch Pharmacol 365(Suppl) 2:R 48.

Levine, et al., *Microsurgical denervation of the spermatic cord as primary surgical treatment of chronic orchialgia*, Journal of Urology, vol. 165, No. 6, Jun. 2001, pp. 1927-1929 (Abst).

Schurch, B., et al., *Botox in urology: a new treatment modality without limitations*? Eau Update Series, vol. 2, No. 4, Dec. 2004, pp. 170-178 (Abst).

Mayo Clinic, *Retractile testicle*, 1998-2009 (web page www.MayoClinic.com).

\* cited by examiner

METHODS FOR ALLEVIATING TESTICULAR PAIN

BACKGROUND

The present invention relates to methods for alleviating a testicular pain. In particular the present invention relates to methods for treating a chronic testicular pain.

A testicular pain (orchialgia) can be a short term condition or a long term condition. When a testicular pain lasts for three months or longer, it is called a chronic testicular pain.

A testicular pain can significantly interfere with the daily activities of the patient. Unfortunately, chronic testicular pain seems to be an increasing problem among the male population (Granitsiotis et al., European Urology (2004) 45:430-436). Moreover, management of the patient with chronic testicular pain is often difficult and occupies a considerable amount of most urologists' time.

Chronic testicular pain may be associated with (e.g., caused by) different etiologies such as trauma, infection, hydrocele, varicocele, testicular tumor, vasectomy. Almost 25% of these cases are of unknown origin. Conventionally, the procedure for alleviating a chronic testicular pain is nonsurgical, which includes the administration of antibiotics, analgesics, anti-inflammatory medications and regional nerve blocks. However, these nonsurgical treatments may not properly alleviate the pain. When the conventional treatment fails, the next course of therapy is unclear. Physicians have attempted radical procedures, e.g., inguinal orchiectomy, to alleviate the pain. However, these radical procedures have limited success. For example, it has been reported that up to 80% of patients undergoing an inguinal orchiectomy do not experience adequate pain relief after the procedure.

Male Genitalia

The male genitals include the testes, the ductus deferentes, the vesiculae seminales, the ejaculatory ducts, the penis, and accessory structures.

The testes are two glandular organs, which secrete the semen. They are suspended in the scrotum by the spermatic cords (FIGS. 1 and 2). The coverings of the testes are the skin, dartos tunic, intercrural fascia, scrotum, cremaster, infundibuliform fascia, tunica vaginalis and intercrural fascia.

The scrotum is a cutaneous pouch which contains the testes and parts of the spermatic cords. It is divided on its surface into two lateral portions by a ridge or raphé, which is continued forward to the under surface of the penis, and backward, along the middle line of the perineum to the anus. Of these two lateral portions the left hangs lower than the right, to correspond with the greater length of the left spermatic cord. The scrotum consists of two layers, the integument and the dartos tunic. The Integument is very thin, of a brownish color, and generally thrown into folds or rugae. It is provided with sebaceous follicles, the secretion of which has a peculiar odor, and is beset with thinly scattered, crisp hairs, the roots of which are seen through the skin. The dartos tunic (tunica dartos) is a thin layer of non-striped muscular fibers, continuous, around the base of the scrotum, with the two layers of the superficial fascia of the groin and the perineum; it sends inward a septum, which divides the scrotal pouch into two cavities for the testes, and extends between the raphé and the under surface of the penis, as far as its root.

The Intercrural Fascia (intercolumnar or external spermatic fascia) is a thin membrane, prolonged downward around the surface of the cord and testis (see page 411). It is separated from the dartos tunic by loose areolar tissue.

The Cremaster consists of scattered bundles of muscular fibers connected together into a continuous covering by intermediate areolar tissue.

The Infundibuliform Fascia (tunica vaginalis communes [testis et funiculi spermatici]) is a thin layer, which loosely invests the cord; it is a continuation downward of the transversalis fascia.

The nerves are the ilioinguinal and lumboinguinal branches of the lumbar plexus, the two superficial perineal branches of the internal pudendal nerve, and the pudendal branch of the posterior femoral cutaneous nerve.

The spermatic Cord (funiculus spermaticus) (FIG. 2) extends from the abdominal inguinal ring, where the structures of which it is composed converge, to the back part of the testis. In the abdominal wall the cord passes obliquely along the inguinal canal, lying at first beneath the obliquus internus, and upon the fascia transversalis; but nearer the pubis, it rests upon the inguinal and lacunar ligaments, having the aponeurosis of the obliquus externus in front of it, and the inguinal faix behind it. It then escapes at the subcutaneous ring, and descends nearly vertically into the scrotum. The left cord is rather longer than the right, consequently the left testis hangs somewhat lower than its fellow.

The spermatic cord is composed of arteries, veins, lymphatics, nerves, and the excretory duct of the testis. These structures are connected together by areolar tissue, and invested by the layers brought down by the testis in its descent.

The nerves are the spermatic plexus from the sympathetic, joined by filaments from the pelvic plexus which accompany the artery of the ductus deferens.

The testes are suspended in the scrotum by the spermatic cords, the left testis hanging somewhat lower than its fellow. The average dimensions of the testis are from 4 to 5 cm. in length, 2.5 cm. in breadth, and 3 cm. in the antero-posterior diameter; its weight varies from 10.5 to 14 gm. Each testis is of an oval form compressed laterally, and having an oblique position in the scrotum; the upper extremity is directed forward and a little lateralward; the lower, backward and a little medialward; the anterior convex border looks forward and downward, the posterior or straight border, to which the cord is attached, backward and upward.

The anterior border and lateral surfaces, as well as both extremities of the organ, are convex, free, smooth, and invested by the visceral layer of the tunica vaginalis. The posterior border, to which the cord is attached, receives only a partial investment from that membrane. Lying upon the lateral edge of this posterior border is a long, narrow, flattened body, named the epididymis.

The epididymis consists of a central portion or body; an upper enlarged extremity, the head (globus major); and a lower pointed extremity, the tail (globus minor, which is continuous with the ductus deferens, the duct of the testis (FIG. 3). The head is intimately connected with the upper end of the testis by means of the efferent ductules of the gland; the tail is connected with the lower end by cellular tissue, and a reflection of the tunica vaginalis. The lateral surface, head and tail of the epididymis are free and covered by the serous membrane; the body is also completely invested by it, excepting along its posterior border; while between the body and the testis is a pouch, named the sinus of the epididymis (digital fossa). The epididymis is connected to the back of the testis by a fold of the serous membrane.

On the upper extremity of the testis, just beneath the head of the epididymis, is a minute oval, sessile body, the appendix of the testis (hydatid of Morgagni); it is the remnant of the upper end of the Müllerian duct. On the head of the epididymis is a second small stalked appendage (sometimes duplicated); it is named the appendix of the epididymis (pedunculated hydatid), and is usually regarded as a detached efferent duct.

The testis is invested by three tunics: the tunica vaginalis, tunica albuginea, and tunica vasculosa. The Tunica Vaginalis (tunica vaginalis propria testis) is the serous covering of the testis. It is a pouch of serous membrane, derived from the saccus vaginalis of the peritoneum, which in the fetus preceded the descent of the testis from the abdomen into the scrotum. After its descent, that portion of the pouch which extends from the abdominal inguinal ring to near the upper part of the gland becomes obliterated; the lower portion remains as a shut sac, which invests the surface of the testis, and is reflected on to the internal surface of the scrotum; hence it may be described as consisting of a visceral and a parietal lamina.

The visceral lamina (lamina visceralis) covers the greater part of the testis and epididymis, connecting the latter to the testis by means of a distinct fold. From the posterior border of the gland it is reflected on to the internal surface of the scrotum.

The parietal lamina (lamina parietalis) is far more extensive than the visceral, extending upward for some distance in front and on the medial side of the cord, and reaching below the testis. The inner surface of the tunica vaginalis is smooth, and covered by a layer of endothelial cells. The interval between the visceral and parietal laminae constitutes the cavity of the tunica vaginalis.

The tunica Albuginea is the fibrous covering of the testis. It is a dense membrane, of a bluish-white color, composed of bundles of white fibrous tissue which interlace in every direction. It is covered by the tunica vaginalis, except at the points of attachment of the epididymis to the testis, and along its posterior border, where the spermatic vessels enter the gland. It is applied to the tunica vasculosa over the glandular substance of the testis, and, at its posterior border, is reflected into the interior of the gland, forming an incomplete vertical septum, called the mediastinum testis (corpus Highmori).

The mediastinum testis extends from the upper to near the lower extremity of the gland, and is wider above than below. From its front and sides numerous imperfect septa (trabeculae) are given off, which radiate toward the surface of the organ, and are attached to the tunica albuginea. They divide the interior of the organ into a number of incomplete spaces which are somewhat cone-shaped, being broad at their bases at the surface of the gland, and becoming narrower as they converge to the mediastinum. The mediastinum supports the vessels and duct of the testis in their passage to and from the substance of the gland.

Botulinum Toxin

The genus *Clostridium* has more than one hundred and twenty seven species, grouped according to their morphology and functions. The anaerobic, gram positive bacterium *Clostridium botulinum* produces a potent polypeptide Clostridial toxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unaffenuated through the lining of the gut and attack peripheral motor neurons. Symptoms of botulism toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified Clostridial toxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1996) (where the stated $LD_{50}$ of type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Available from Allergan, Inc., of Irvine, Calif. under the tradename BOTOX® in 100 unit vials Seven immunologically distinct botulinum Clostridial toxins have been characterized, these being respectively botulinum Clostridial toxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus Clostridial toxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin). which cleave the same bond.

Although all the botulinum toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Gonelle-Gispert, C., et al., *SNAP-25a and-25b isoforms are both expressed in insulin-secreting cells and can function in insulin secretion*, Biochem J. 1;339 (pt 1):159-65:1999, and Boyd R. S. et al., *The effect of botulinum Clostridial toxin-B on insulin release from a ∃-cell line*, and Boyd R. S. et al., *The insulin secreting ∃-cell line, HIT-15, contains SNAP-25 which is a target for botulinum Clostridial toxin-A*, both published at *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant Clostridial toxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for a lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy.

Botulinum toxins and toxin complexes can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include BOTOX® (Botulinum toxin type A Clostridial toxin complex with human serum albumin and sodium chloride) available from Allergan, Inc., of Irvine, Calif. in 100 unit vials as a lyophilized powder to be reconstituted with 0.9% sodium chloride before use), Dysport® (Clostridium botulinum type A toxin haemagglutinin complex with human serum albumin and lactose in the formulation), available from Ipsen Limited, Berkshire, U.K. as a powder to be reconstituted with 0.9% sodium chloride before use), and MyoBoc™ (an injectable solution comprising botulinum toxin type B, human serum albumin, sodium succinate, and sodium chloride at about pH 5.6, available from Elan Corporation, Dublin, Ireland).

The success of botulinum toxin type A to treat a variety of clinical conditions has led to interest in other botulinum toxin serotypes. Additionally, pure botulinum toxin has been used to treat humans. see e.g. Kohl A., et al., *Comparison of the effect of botulinum toxin A (BOTOX (R)) with the highly-purified Clostridial toxin (NT201) in the extensor digitorum brevis muscle test*, Mov Disord 2000;15(Suppl 3):165. Hence, a pharmaceutical composition can be prepared using a pure botulinum toxin.

The type A botulinum toxin is known to be soluble in dilute aqueous solutions at pH 4-6.8. At pH above about 7 the stabilizing nontoxic proteins dissociate from the Clostridial toxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Clostridial toxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1987). Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Clostridial toxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [$^3$H]Noradrenaline and [$^3$H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by non-proteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3\times10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Clostridial toxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of 1-2×10$^8$ LD$_{50}$ U/mg or greater; purified botulinum toxin type B with an approximately 156 kD molecular weight with a specific potency of 1-2×10$^8$ LD$_{50}$ U/mg or greater, and; purified botulinum toxin type F with an approximately 155 kD molecular weight with a specific potency of 1-2×10$^7$ LD$_{50}$ U/mg or greater.

Either the pure botulinum toxin (i.e. the 150 kilodalton botulinum toxin molecule) or the toxin complex can be used to prepare a pharmaceutical composition. Both molecule and complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of Clostridium botulinum toxin type A purified Clostridial toxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology,* 48:249-53:1997.

Botulinum toxins have been used in clinical settings for the treatment of neuromuscular disorders characterized by hyperactive skeletal muscles. Botulinum toxin type A (BOTOX®) was approved by the U.S. Food and Drug Administration in 1989 for the treatment of essential blepharospasm, strabismus and hemifacial spasm in patients over the age of twelve. In 2000 the FDA approved commercial preparations of type A (BOTOX®) and type B botulinum toxin (MYOBLOC®) serotypes for the treatment of cervical dystonia, and in 2002 the FDA approved a type A botulinum toxin (BOTOX®) for the cosmetic treatment of certain hyperkinetic (glabellar) facial wrinkles. Clinical effects of peripheral intramuscular botulinum toxin type A are usually seen within one week of injection and sometimes within a few hours. The typical duration of symptomatic relief (i.e. flaccid muscle paralysis) from a single intramuscular injection of botulinum toxin type A can be about three months, although in some cases the effects of a botulinum toxin induced denervation of a gland, such as a salivary gland, have been reported to last for several years. For example, it is known that botulinum toxin type A can have an efficacy for up to 12 months (Naumann M., et al., Botulinum toxin type A in the treatment of focal, axillary and palmar hyperhidrosis and other hyperhidrosis and other hyperhidrotic conditions, European J. Neurology 6 (Supp 4):S111-S115:1999), and in some circumstances for as long as 27 months. Ragona, R. M., et al., Management of parotid sialocele with botulinum toxin, The Laryngoscope 109:1344-1346:1999. However, the usual duration of an intramuscular injection of BOTOX® is typically about 3 to 4 months.

It has been reported that a botulinum toxin type A has been used in diverse clinical settings, including for example as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Lyons, J., et al., *Tremor-Predominant Parkinson's Disease*, Drugs & Aging 16(4); 273-278:2000.

Treatment of certain gastrointestinal and smooth muscle disorders with a botulinum toxin are known. See e.g. U.S. Pat. Nos. 5,427,291 and 5,674,205 (Pasricha). Additionally, transurethral injection of a botulinum toxin into a bladder sphincter to treat a urination disorder is known (see e.g. Dykstra, D. D., et al, *Treatment of detrusor-sphincter dyssynergia with botulinum A toxin: A double-blind study*, Arch Phys Med Rehabil 1990 January; 71:24-6), as is injection of a botulinum toxin into the prostate to treat prostatic hyperplasia. See e.g. U.S. Pat. No. 6,365,164 (Schmidt).

U.S. Pat. No. 5,766,605 (Sanders) proposes the treatment of various autonomic disorders, such as excessive stomach acid secretion, hypersalivation, rhinittis, with a botulinum toxin. Additionally, it is known that nasal hypersecretion is predominantly caused by over activity of nasal glands, which are mainly under cholinergic control and it has been demonstrated that application of botulinum toxin type A to mammalian nasal mucosal tissue of the maxillary sinus turbinates can induce a temporary apoptosis in the nasal glands. Rohrbach S., et al., *Botulinum toxin type A induces apoptosis in nasal glands of guinea pigs*, Ann Otol Rhinol Laryngol 2001 November; 110(11):1045-50. Furthermore, local application of botulinum toxin A to a human female patient with intrinsic rhinitis resulted in a clear decrease of the nasal hypersecretion within five days. Rohrbach S., et al., *Minimally invasive application of botulinum toxin type A in nasal hypersecretion*, J Oto-Rhino-Laryngol 2001 November-December; 63(6):382-4.

Various afflictions, such as hyperhydrosis and headache, treatable with a botulinum toxin are discussed in WO 95/17904 (PCT/US94/14717) (Aoki). EP 0 605 501 B1 (Graham) discusses treatment of cerebral palsy with a botulinum toxin and U.S. Pat. No. 6,063,768 (First) discusses treatment of neurogenic inflammation with a botulinum toxin.

In addition to having pharmacologic actions at the peripheral location, botulinum toxins can also have inhibitory effects in the central nervous system. Work by Weigand et al, ([125]*I-labelled botulinum A Clostridial toxin:pharmacokinetics in cats after intramuscular injection*, Nauny-Schmiedeberg's. Arch. Pharmacol. 1976; 292,161-165), and Habermann, ([125]*I-labelled Clostridial toxin from clostridium botulinum A: preparation, binding to synaptosomes and ascent to the spinal cord*, Nauny-Schmiedeberg's Arch. Pharmacol. 1974; 281, 47-56) showed that botulinum toxin is able to ascend to the spinal area by retrograde transport. As such, a botulinum toxin injected at a peripheral location, for example intramuscularly, may be retrograde transported to the spinal cord.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

U.S. Pat. No. 5,989,545 discloses that a modified Clostridial toxin or fragment thereof, preferably a botulinum toxin, chemically conjugated or recombinantly fused to a particular targeting moiety can be used to treat pain by administration of the agent to the spinal cord.

A botulinum toxin has also been proposed for the treatment of hyperhydrosis (excessive sweating, U.S. Pat. No. 5,766,605), headache, (U.S. Pat. No. 6,458,365, migraine headache (U.S. Pat. No. 5,714,468), post-operative pain and visceral pain (U.S. Pat. No. 6,464,986), pain by intraspinal administration (U.S. Pat. No. 6,113,915), Parkinson's disease by intracranial administration (U.S. Pat. No. 6,306,403), hair growth and hair retention (U.S. Pat. No. 6,299,893), psoriasis and dermatitis (U.S. Pat. No. 5,670,484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a botulinum toxin into the upper and lower esophageal, pyloric and anal sphincters) ), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (U.S. Pat. Nos. 6,306,423 and 6,312,708).

Cakmak et al. (2003) Urol Res 31:352-354 reported an injection of a botulinum toxin to a cremaster muscle (which envelops the testicle) to treat a retractile testis. Westhoff et al. (2002) Naunyn Schmiedebergs Arch Pharmacol 365(Suppl) 2:R 48 reported an injection of a botulinum Toxin to an iliopsoas muscle (the muscle that starts at the lower back and inserts into the thigh bone (femur) to treat symptoms such as groin pain. However, neither Cakmak nor Westhoff teaches or suggests that a botulinum toxin can be administered to the testicle or tissues connected with the testicle to treat a testicular pain.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmifters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Clostridial toxin Type A and Comparison with Other Clostridial toxins*, J Biological Chemistry 265(16); 9153-9158:1990.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

As discussed above, the conventional procedures for treating testicular pain have a low success rate for alleviating the pain.

What is needed therefore is an improved method for alleviating testicular pain.

SUMMARY

The present invention meets this need and provides for improved methods for alleviating a testicular pain. In some embodiments, the methods comprise the step of locally administering a neurotoxin (e.g., a botulinum toxin type A and/or other types) to at least one anatomical site selected from the group consisting of a testicle and a tissue associated with the testicle. As defined herein, a "tissue associated with the testicle" is a tissue which is physically connected to the testicle or a tissue that can functionally affect the testicle. A "tissue associated with the testicle" can be a connective tissue, a muscle tissue or a nerve tissue. For example, a tissue associated with the testicle comprises at least one of a vas deferens, an epididymis, or a spermatic cord.

In some embodiments, a tissue associated with the testicle comprises at least one nerve tissue selected from the group consisting of a nerve innervating the testicle and a nerve plexus innervating the testicle. For example, a tissue associated with the testicle comprises at least one a nerve tissue selected from the group consisting of an ilioinguinal nerve branch of the lumbar plexus, a lumboinguinal nerve branch of the lumbar plexus, a superficial perineal nerve branch of the internal pudendal nerve, a pudendal nerve branch of the posterior femoral cutaneous nerve and a filament of spermatic plexus.

In some embodiments, the testicular pain that is alleviated by the present methods is a chronic testicular pain. In some embodiments, the present methods are effective to treat a pain that is caused by orchitis. In some embodiments, the present methods are effective to treat a pain that is caused by an epidimymitis. In some embodiments, the present methods are effective to treat a pain that is caused by an obstruction of the vas deferens. In some embodiments, the present methods are effective to treat a pain that is caused by a spasm of the vas deferens. In some embodiments, the present methods are effective to treat a pain that is caused by a surgery (e.g., post vasectomy pain syndrome).

In some embodiments, the present methods comprise the step of administering a neurotoxin (e.g., botulinum toxin) to a cremaster muscle to alleviate a testicular pain that is not caused by a retractile of the testis. In some embodiments, the present invention excludes the administration of a botulinum toxin to a cremaster muscle to alleviate a testicular pain due to retractile testis.

In some embodiments, the dose of neurotoxin to be administered is equivalent to about 1 unit to about 500 units of a botulinum toxin type A.

The term "neurotoxin" employed herein refers to one or more of a toxin made by a bacterium, for example, a *Clostridium botulinum, Clostridium butyricum, Clostridium beratti, Clostridium tetani*. In some embodiments, the neurotoxin is a botulinum toxin. The botulinum toxin may be a botulinum toxin type A (including $A_1$ or $A_2$), type B, type $C_1$, type D, type E, type F, or type G. In some embodiments, the neurotoxin is a botulinum toxin type A. Unless stated otherwise, the dose of the neurotoxin referenced herein is equivalent to that of a botulinum toxin type A. The assays required to determine equivalency to the therapeutic effectiveness of botulinum toxin type A at a certain dosage are well established.

Further, the botulinum toxin of the present invention may comprise a first element comprising a binding element able to specifically bind to a neuronal cell surface receptor under physiological conditions; a second element comprising a translocation element able to facilitate the transfer of a polypeptide across a neuronal cell membrane, and a third element comprising a therapeutic element able, when present in the cytoplasm of a neuron, to inhibit exocytosis of acetylcholine from the neuron. The therapeutic element can cleave a SNARE protein, thereby inhibiting the exocytosis of acetylcholine from the neuron. The SNARE protein can be selected from the group consisting of syntaxin, SNAP-25 and VAMP.

Definitions

The following definitions apply herein.

"About" means plus or minus ten percent of the value so qualified.

"Alleviate" as applied to pain means a reduction of pain. In some embodiments, the reduction of pain is reduced by more than 25%. In some embodiments, the reduction of pain is by more than 50%. The reduction of pain is measured by the patient reporting the degree of pain after the neurotoxin treatment as compared to the degree of pain prior to the treatment.

"Effective amount" as applied to the neurotoxin means that amount of the neurotoxin generally sufficient to effect a desired change in the subject. For example, where the desired effect is decreasing the spasm of a vas deferens, an effective amount of the compound is that amount which causes at least a decrease in the spasm of the vas deferens by more than 30%. In some embodiments, the neurotoxin can be administered in an amount between about 0.01 U/kg and about 35 U/kg and the pain treated can be substantially alleviated for between about 1 month and about 27 months, for example for from about 1 month to about 6 months.

"Locally administering" or "local administration" means direct injection to an organ (e.g., testicle) and/or a tissue (e.g., tissue associated with a testicle, defined below). Local administration excludes systemic routes of administration, such as intravenous or oral administration.

A "tissue associated with the testicle" is a tissue which is physically connected to the testicle or a tissue that can functionally affect the testicle. A "tissue associated with the testicle" can be a connective tissue, a muscle tissue or a nerve tissue.

DRAWINGS

FIG. 1 shows the scrotum. On the left side, the cavity of the tunica vaginalis has been opened. On the right side, only the layers superficial to the Cremaster have been removed.

FIG. 2 shows a scrotum where the penis has been turned upward, and the anterior wall of the scrotum has been removed. On the right side, the spermatic cord, the infundibuliform fascia, and the Cremaster muscle are displayed. On the left side, the infundibuliform fascia has been divided by a longitudinal incision passing along the front of the cord and the testicle, and a portion of the parietal layer of the tunica vaginalis has been removed to display the testicle and a portion of the head of the epididymis, which are covered by the visceral layer of the tunica vaginalis.

DESCRIPTION

The present invention is partly based upon the surprising discovery that an administration of a neurotoxin, such as a botulinum toxin type A or other types, to a testicle or a tissue associated with a testicle can alleviate a pain that the patient experiences at the testicle.

In some embodiments, the methods comprise the step of locally administering a neurotoxin (e.g., a botulinum toxin) to at least one anatomical site selected from the group consisting of a testicle and a tissue associated with the testicle. As defined herein, a "tissue associated with the testicle" is a tissue which is connected to the testicle or a tissue that can functionally affect the testicle. A "tissue associated with the testicle" can be a connective tissue, a muscle tissue or a nerve tissue. For example, a tissue associated with the testicle comprises at least one of a vas deferens, an epididymis, or a spermatic cord.

In some embodiments, a tissue associated with the testicle comprises at least one nerve tissue selected from the group consisting of a nerve innervating the testicle and a nerve plexus innervating the testicle. For example, a tissue associated with the testicle comprises at least one a nerve tissue selected from the group consisting of an ilioinguinal nerve branch of the lumbar plexus, a lumboinguinal nerve branch of the lumbar plexus, a superficial perineal nerve branch of the internal pudendal nerve, a pudendal nerve branch of the posterior femoral cutaneous nerve and a filament of spermatic plexus.

The present methods are effective to treat a chronic testicular pain, i.e., pain lasting for more than three months. For example, a surgery such as a vasectomy can cause a pain that lasts for more than three months, e.g., post vasectomy pain syndrome. In some embodiments, the post vasectomy pain syndrome can be treated by the administration of a neurotoxin (e.g., botulinum toxin type A, or other types) to a spermatic cord. Without wishing to limit the invention to any theory or mechanism of operation, it is believed that the administration of a neurotoxin to the spermatic cord can decrease the transmission of pain signal, thereby alleviating the testicular pain.

Figure 2:
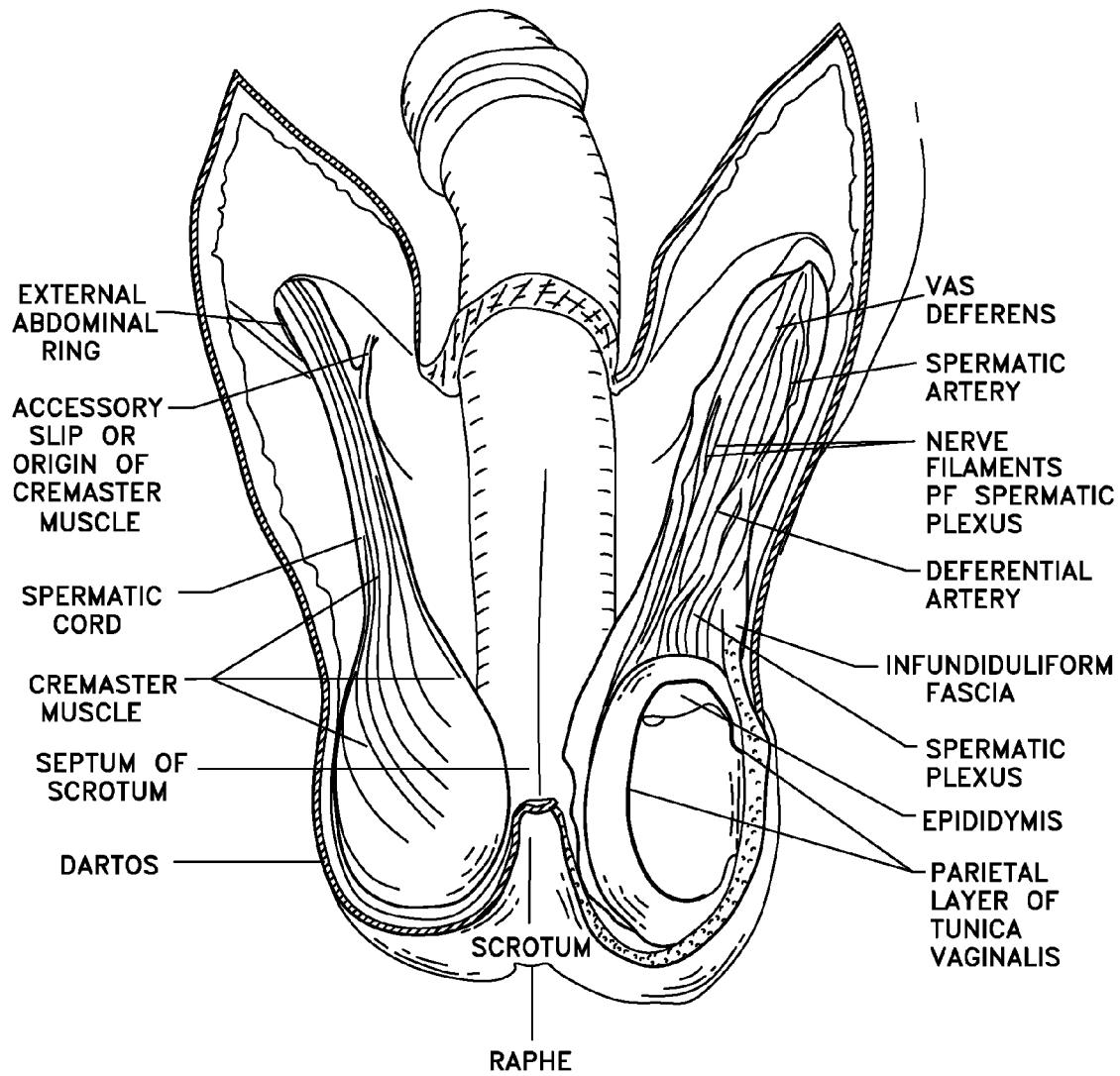
Figure 3:
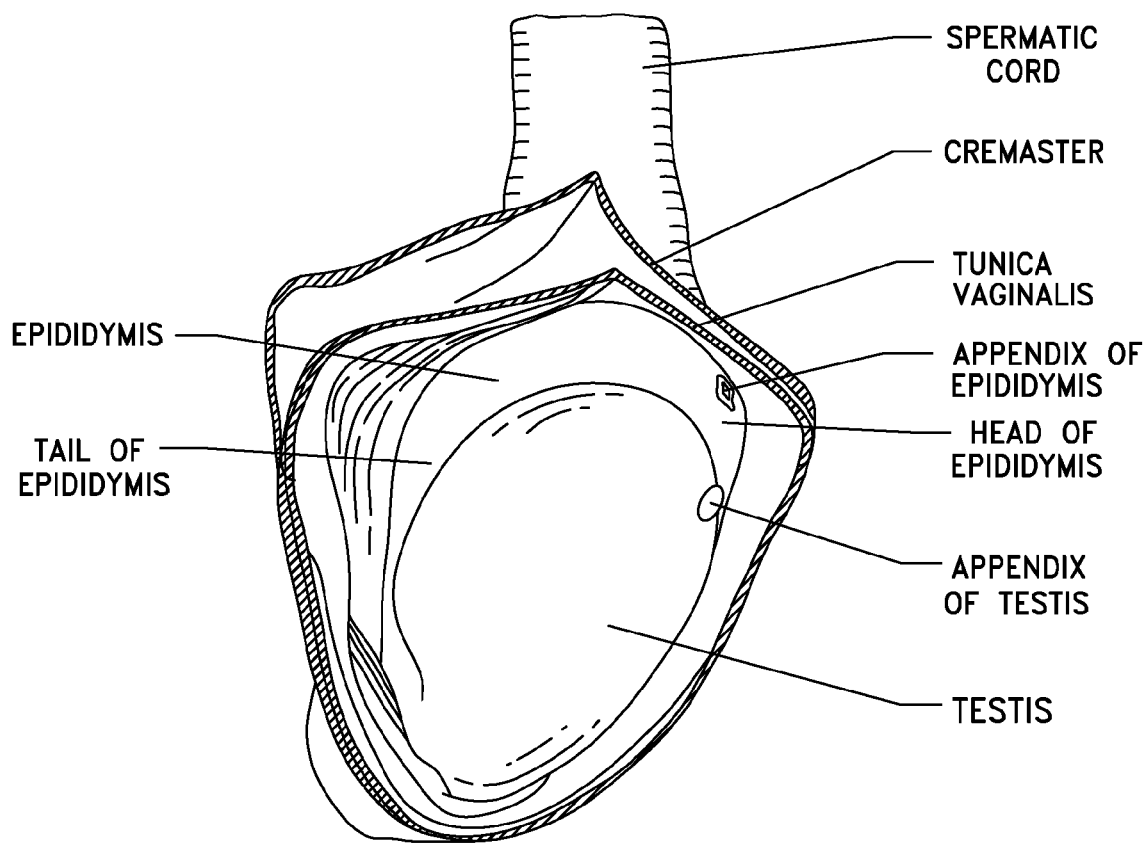
FIG. 3 shows the right testis, exposed by laying open the tunica vaginalis.

The present methods are effective to treat a pain that is caused by an inflammation of the testicle (orchitis) or the epididymis (epidimymitis). In some embodiments, the pain can be alleviated by a local administration of a neurotoxin (e.g., botulinum toxin type A, or other types) to the testicle and/or the epididymis (FIG. 2). In some embodiments, the neurotoxin is administered to the posterior side of the testicle. Further, the neurotoxin can be administered to multiple sites on the testicle, for example, sites being about 1 cm apart. In some embodiments, the neurotoxin is administered to the epididymis. Moreover, the neurotoxin can be administered to multiple sites on the epididymis, for example, sites being about 1 cm apart. Without wishing to limit the invention to any theory or mechanism of operation, it is believed that the administered neurotoxin is effective to inhibit the release of pro-inflammation cytokines, thereby reducing the pain.

In certain cases, the testicular pain is due to a spasm of the vas deferens. In some embodiments, a neurotoxin can be administered to the vas deferens to treat the testicular pain.

In some embodiments, the present method comprises the step of administering a neurotoxin (e.g., botulinum toxin) to a cremaster muscle to alleviate a testicular pain that is not caused by a retractile of the testis. In some embodiments, the present invention excludes the administration of a botulinum toxin to a cremaster muscle to alleviate a testicular pain due to retractile testis.

In some embodiments, the dose of a neurotoxin administered is equivalent to about 1 unit to about 500 units of a botulinum toxin type A. In some embodiments, the dose of a neurotoxin administered is equivalent to about 1 unit to about 300 units of a botulinum toxin type A. In some embodiments, the dose of a neurotoxin administered is equivalent to about 1 unit to about 150 units of a botulinum toxin type A. In some embodiments, the dose of a neurotoxin administered is equivalent to about 1 unit to about 75 units of a botulinum toxin type A. In some embodiments, the dose of a neurotoxin administered is equivalent to about 1 unit to about 40 units of a botulinum toxin type A. In some embodiments, the dose of a neurotoxin administered is in an amount of between about 0.1 unit and about 5 units. In some embodiments, a neurotoxin, such as a botulinum toxin type A or other types, can be locally administered according to the present disclosed methods in amounts of between about $10^{-3}$ U/kg to about 10 U/kg. In some embodiments, a neurotoxin, such as a botulinum toxin type A or other types, can be locally administered according to the present disclosed methods in amounts of between about $10^{-2}$ U/kg and about 1 U/kg. In some embodiments, a neurotoxin, such as a botulinum toxin type A or other types, can be locally administered according to the present disclosed methods in amounts of between about $10^{-1}$ U/kg and about 1 U/kg. Significantly, the pain alleviating effect of the present disclosed methods can persist for between about 2 months to about 6 months.

Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

In some embodiments, the neurotoxin is administered to a "patient in need thereof", which means that the patient has been specifically diagnosed as having a testicle pain and the neurotoxin is administered for the specific purpose of alleviating the testicular pain.

Preferably, a neurotoxin used to practice a method within the scope of the present invention is a botulinum toxin, such as one of the serotype A (including $A_1$ and $A_2$), B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope: (a) Clostridial toxin complex as well as pure Clostridial toxin obtained or processed by bacterial culturing, toxin extraction, concentration, preservation, freeze drying and/or reconstitution and; (b) modified or recombinant Clostridial toxin, that is Clostridial toxin that has had one or more amino acids or amino acid sequences deliberately deleted, modified or redeployed by known chemical/biochemical amino acid modification procedures or by use of known host cell/recombinant vector recombinant technologies, as well as derivatives or fragments of Clostridial toxins so made, and includes Clostridial toxins with one or more attached targeting moieties for a cell surface receptor present on a cell.

Neurotoxins, e.g., botulinum toxins, for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

EXAMPLES

The following examples set forth specific methods encompassed by the present invention and are not intended to limit the scope of the present invention.

Example 1

Methods for Alleviating Testicular Pain by Administering to a Testicle

An administration of a neurotoxin such as a botulinum toxin type A or other types to a testicle can be effective to alleviate, for example, a pain caused by orchitis.

Orchitis is an inflammation of one or both testis, accompanied by swelling, pain, fever, and a sensation of heaviness in the affected area.

Viral mumps is the most common cause of orchitis. Bacterial infections associated with the disorder are tuberculosis, syphilis, gonorrhea, and chlamydia. A mechanical injury to the groin area may also cause orchitis. Fifteen to twenty-five percent of males past the age of puberty with mumps develop orchitis. Epididymo-orchitis (inflammation of both testis and part of the spermatic duct) is the most common bacterial type of Orchitis. This form of the condition occurs most often in sexually active males fifteen years and older, and in men over 45 with enlarged prostates.

The people most susceptible to orchitis are those with inadequate mumps inoculation and, in the case of sexually transmitted orchitis, those who practice unsafe sex or have a history of sexually transmitted disease. Inadequate protection of the groin area during contact sports or other potentially harmful physical activities may result in injury leading to orchitis.

A twenty year old male patient presents with orchitis of the left testicle. His symptoms include swelling of the left testicle, tenderness in the groin area, fever, headache, nausea, bloody discharge from the penis, and pain during urination, intercourse, or ejaculation. Blood test shows the cause of the orchitis to be bacterial infection (gonorrhea). The patient reports that he has pain in the testicle for over four months, and has to take many days off from work.

The treating physician administers about 0.10 to about 10 units of a neurotoxin (e.g., botulinum toxin type A) directly to the patient's left testicle. Without wishing to limit the invention to any theory or mechanism of operation, it is believed that an administration of the neurotoxin to the testicle reduces the release of pro-inflammatory cytokines, e.g., interleukin 6 and interleukin 8, within the testicle region. It is further believed that the reduction of these inflammation factors can alleviate the pain. Alternatively, or additionally, the physician may also administer about 0.10 to about 10 units of a neurotoxin (e.g., botulinum toxin type A) to the patient's epididymis.

About five days after the administration of the neurotoxin, the patient reports that the pain in the testicle is alleviated by about 30%. The patient also reports and improvement for the other orchitis symptoms.

Example 2

Methods for Alleviating Testicular Pain by Administering to a Tissue Connected with a Testicle An administration of a neurotoxin such as a botulinum toxin type A or other types to a tissue connected with a testicle may be effective to alleviate, for example, a pain caused by surgery (e.g. postvasectomy pain syndrome).

Postvasectomy pain syndrome represents a very specific cause of chronic testicular pain. The etiology is unknown with commonly cited causes as spasm of the vas deferens, dilatation of epididymal tubule, inflammation, perineural fibrosis, sperm extravasation or yet unidentified process. Postvasectomy pain syndrome occurs in about 15-19% of patients who has had a vasectomy (Granitsiotis et al., European Urology (2004) 45:430-436, at page 431).

A 35 year old male patient is diagnosed as having a postvasectomy pain syndrome in the right testicle. The treating physician administers about 0.10 to about 10 units of a neurotoxin (e.g., botulinum toxin type A) directly to the patient's vas deferens to alleviate the pain.

Figure 4:
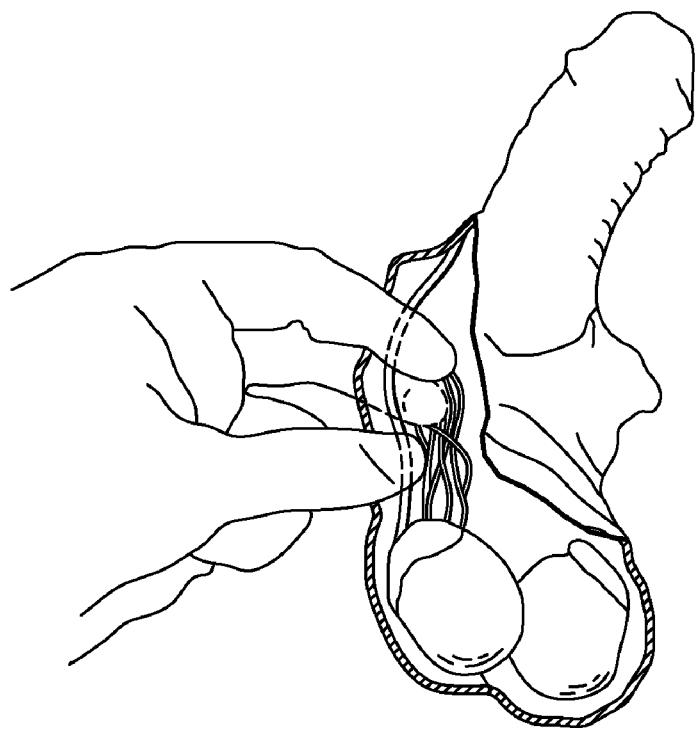
FIG. 4 shows a three-finger technique for isolation of the vas deferens.
Figure 4A:
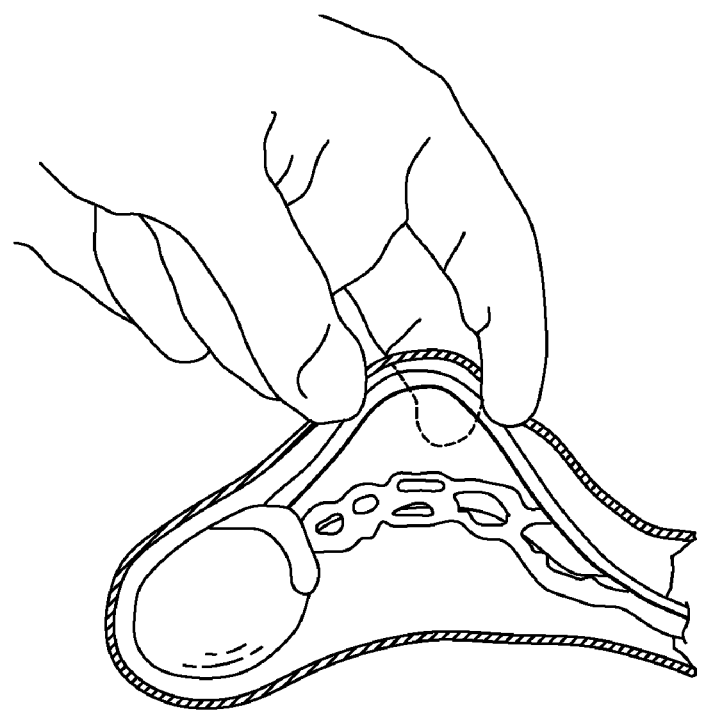

The neurotoxin administration procedure begins with isolation of the vas deferens using the three-finger technique (FIG. 4). Starting on the patient's right side, the middle finger of the left of the physician's hand is placed beneath the scrotum and the spermatic cord structures are drawn from the mid-line laterally until the vas deferens is trapped between the middle finger the thumb and the index finger. The location of the thumb is just below the optimal site for the puncture wound. The middle finger elevates and isolates the vas. The index finger stabilizes the vas. Once the vas is firmly fixed using the three-finger technique, the physician administers the neurotoxin to the vas, preferably to the wall of the vas.

Without wishing to limit the invention to any theory of mechanism of operation, it is believed that the administration of a neurotoxin (e.g., botulinum toxin) to the vas deferens reduces the spasm of the vas deferens to alleviate the pain.

About one week after the administration of the neurotoxin, the patient reports that the pain in the testicle is alleviated by about 50%. One month after the administration, the patient reports that the pain is alleviated by more than 75%.

Example 3

Methods for Alleviating Testicular Pain by Administering to a Nerve Innervating the Testicle An administration of a neurotoxin such as a botulinum toxin type A or other types to a nerve innervating the testicle may be effective to alleviate, for example, a referred pain.

Chronic testicular pain may be a referred pain. Any organ that shares the same nerve pathway with the scrotal contents can present pain in the testicular region. Pain arising in the ureter, hip, intervertebral disc prolapse and entrapment neuropathies of the ilioinginal or genitofemoral nerve, often due to inguinal hernias or following their repair are some of the secondary causes of chronic testicular pain.

A patient is diagnosed as having a referred chronic testicular pain, resulting from an intervertebral disc prolapse. The treating physician administers about 0.10 to about 10 units of a neurotoxin (e.g., botulinum toxin type A) directly to the patient's spermatic cord to alleviate the pain. The administration may be achieved using a technique similar to the three-finger technique of Example 3, where the physician isolates the spermatic cord and administer the neurotoxin thereto.

Preferably, the physician administers the neurotoxin specifically to a nerve filament of a spermatic nexus within the spermatic cord (FIG. 2) to treat the pain.

Example 4

Methods for Alleviating Testicular Pain by Administering to a Nerve Plexus Innervating the Testicle of the Patient An administration of a neurotoxin such as a botulinum toxin type A or other types to a nerve plexus innervating the testicle innervating the testicle may be effective to alleviate, for example, a pain caused trauma to the testicle.

Testicular trauma is relatively uncommon, despite the exposed position of the testicles in the male perineum. Testicular injuries can be divided into 3 broad categories based on the mechanism of injury. These categories include (1) blunt trauma, (2) penetrating trauma, and (3) degloving trauma. Injuries typically occur in men aged 15-40 years.

A careful history and detailed physical examination are essential for an accurate diagnosis. Scrotal ultrasound with Doppler studies is particularly helpful in determining the nature and extent of injury. Penetrating testicular trauma usually requires scrotal exploration to determine the severity of testicular injury, to assess the structural integrity of the testis, and to control intrascrotal hemorrhage. If the tunica albuginea is violated, early surgical exploration, debridement, and closure of the tunica albuginea are necessary.

Patients typically present to the emergency department with a fairly straightforward history of injury (e.g., sports injury, kick to the groin, gunshot wound) soon after the event occurs.

A patient is diagnosed with testicular pain due to blunt trauma to the testicle. The patient exhibits symptoms of severe scrotal pain, nausea and vomiting. Physical examination reveals a swollen, severely tender testicle with visible hematoma. Scrotal or perineal ecchymosis may be present.

The treating physician administers about 0.10 to about 10 units of a neurotoxin (e.g., botulinum toxin type A) directly to the patient's spermatic nexus (FIG. 2) to alleviate the pain.

About one week after the administration of the neurotoxin, the patient reports that the pain in the testicle is alleviated by about 50%. One month after the administration, the patient reports that the pain is alleviated by more than 75%.

Methods according to the invention disclosed herein have many advantages, including the following:

All references, articles, publications and patents and patent applications cited herein are incorporated by reference in their entireties. Other U.S. patents that are incorporated herein by reference include U.S. Pat. Nos. 6,464,986; 6,869,610; 6,887,476; 6,113,915; 6,372,226; 6,235,289; 6,333,037; 5,714,468; 6,776,991 and U.S. Publication No. US 2005-0112147 A1.

Although the present invention has been described in detail with regard to certain preferred methods, other embodiments, versions, and modifications within the scope of the present invention are possible. For example, a wide variety of Clostridial toxins can be effectively used in the methods of the present invention. Additionally, the present invention includes formulations where two or more botulinum toxins, are administered concurrently or consecutively. For example, botulinum toxin type A can be administered until a loss of clinical response or neutralizing antibodies develop, followed by administration also by a botulinum toxin type B or E. Alternately, a combination of any two or more of the *botulinum* serotypes A-G can be locally administered to control the onset and duration of the desired therapeutic result. Furthermore, non-Clostridial toxin compounds can be administered prior to, concurrently with or subsequent to administration of the Clostridial toxin so as to provide an adjunct effect such as enhanced or a more rapid onset of denervation before the Clostridial toxin, such as a botulinum toxin, begins to exert its therapeutic effect.

Accordingly, the spirit and scope of the following claims should not be limited to the descriptions of the preferred embodiments set forth above.

What is claimed is:

1. A method for alleviating a testicular pain, the method comprising the step of locally administering to a human patient in need thereof a botulinum toxin to at least one anatomical site selected from the group consisting of:
   (a) a testicle; and
   (b) a tissue associated with the testicle;
   thereby alleviating the testicular pain.

2. The method of claim 1 wherein the tissue associated with the testicle comprises a connective tissue, a muscle tissue or a nerve tissue.

3. The method of claim 1 wherein the tissue associated with the testicle comprises a vas deferens, an epididymis, and a spermatic cord.

4. The method of claim 1 wherein the botulinum toxin is administered to a vas deferens.

5. The method of claim 1 wherein the botulinum toxin is administered to an epididymis.

6. The method of claim 1 wherein the botulinum toxin is administered to a spermatic cord.

7. The method of claim 1 wherein the tissue associated with the testicle comprises at least one nerve tissue selected from the group consisting of a nerve innervating the testicle and a nerve plexus innervating the testicle.

8. The method of claim 1 wherein the tissue associated with the testicle comprises at least one nerve tissue selected from the group consisting of an ilioinguinal nerve branch of the lumbar plexus, a lumboinguinal nerve branch of the lumbar plexus, a superficial perineal nerve branch of the internal pudendal nerve, a pudendal nerve branch of the posterior femoral cutaneous nerve and a filament of spermatic plexus.

9. The method of claim 1 wherein the tissue associated with the testicle comprises a spermatic plexus.

10. The method of claim 1 wherein the botulinum toxin is selected from the group consisting of botulinum toxin types A, B, $C_1$, D, E, F and G.

11. The method of claim 1 wherein the botulinum toxin is a botulinum toxin type A.

12. The method of claim 1 wherein the botulinum toxin is a botulinum toxin type $A_1$ or $A_2$.

13. The method of claim 1 wherein the pain is a chronic testicular pain.

14. The method of claim 1 wherein the pain is caused by orchitis.

15. The method of claim 1 wherein the pain is caused by an epidimymitis.

16. The method of claim 1 wherein the pain is caused by an obstruction of the vas deferens.

17. The method of claim 1 wherein the pain is caused by a spasm of the vas deferens.

18. The method of claim 1 wherein the pain is a post vasectomy pain syndrome.

19. A method for alleviating a testicular pain to a patient in need thereof, the method comprising the step of locally administering to a human patient in need thereof a botulinum toxin to at least one anatomical site selected from the group consisting of a testicle, vas deferens, an epididymis, and a spermatic cord, an ilioinguinal branch of the lumbar plexus, a lumboinguinal branch of the lumbar plexus, a superficial perineal branch of the internal pudendal nerve, a pudendal branch of the posterior femoral cutaneous nerve, and a filament of spermatic plexus, thereby alleviating the testicular pain.

20. A method for alleviating a post vasectomy testicular pain, the method comprising the step of locally administering to a human patient in need thereof a botulinum toxin to a spermatic cord, thereby alleviating the testicular pain.

21. The method of claim 20 wherein the botulinum toxin is selected from the group consisting of botulinum toxin types A, B, $C_1$, D, E, F and G.

22. The method of claim 20 wherein the botulinum toxin is a botulinum toxin type A.

23. The method of claim 20 wherein the botulinum toxin is a botulinum toxin type $A_1$ or $A_2$.

24. A method for alleviating a testicular pain, the method comprising the step of administering to a human patient in need thereof between about 1 unit and about 500 units of a botulinum toxin to at least one anatomical site selected from the group consisting of a testicle and a tissue associated with the testicle, thereby alleviating the testicular pain.

25. The method of claim 24 wherein the botulinum toxin is selected from the group consisting of botulinum toxin types A, B, $C_1$, D, E, F and G.

26. The method of claim 24 wherein the botulinum toxin is a botulinum toxin type A.

* * * * *

UNITED STATES PATENT AND TRADEMARK OFFICE
CERTIFICATE OF CORRECTION

| | | |
|---|---|---|
| PATENT NO. | : 7,811,586 B2 | |
| APPLICATION NO. | : 11/417335 | |
| DATED | : October 12, 2010 | |
| INVENTOR(S) | : Gregory F. Brooks | |

It is certified that error appears in the above-identified patent and that said Letters Patent is hereby corrected as shown below:

On page 2, in column 1, under "Other Publications", line 17, delete "Nauny-Schmiedeberg's" and insert -- Naunyn-Schmiedeberg's --, therefor.

On page 2, in column 2, under "Other Publications", line 25, delete "Nauny-Schmiedeberg's" and insert -- Naunyn-Schmiedeberg's --, therefor.

Figure 1:
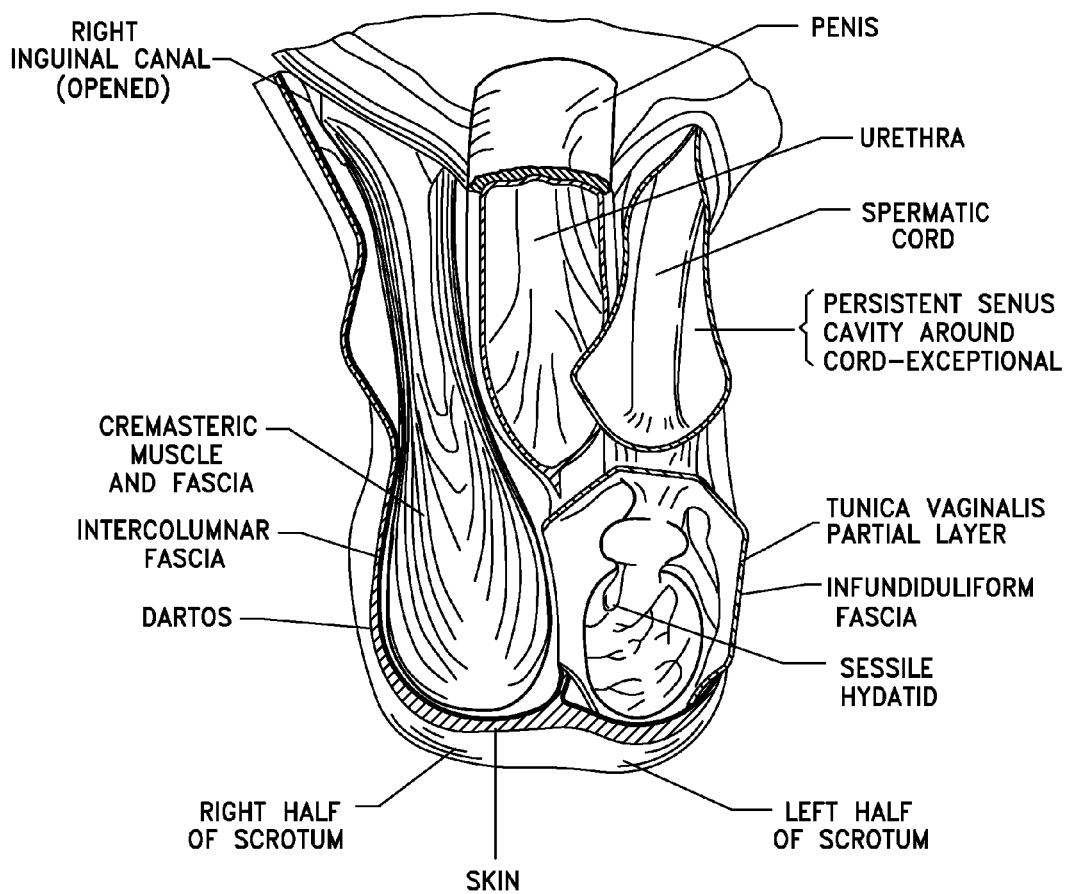

In the drawings:
On Sheet 1 of 4, FIG. 1, line 10, delete "INFUNDIDULIFORM" and insert
-- INFUNDIBULIFORM --, therefor.

On Sheet 2 of 4, FIG. 2, line 11, delete "INFUNDIDULIFORM" and insert
-- INFUNDIBULIFORM --, therefor.

In column 2, line 20, delete "faix" and insert -- falx --, therefor.

In column 2, line 52, delete "minor," and insert -- minor), --, therefor.

In column 3, line 66, delete "unaftenuated" and insert -- unattenuated --, therefor.

In column 4, line 17, after "of" insert -- botulinum toxin --.

In column 4, line 39, delete "lnc." and insert -- Inc. --, therefor.

In column 5, line 18, delete "toxin)." and insert -- toxin) --, therefor.

In column 5, line 57, delete "hemaglutinin" and insert -- hemagglutinin --, therefor.

In column 5, line 58, delete "nonhemaglutinin" and insert -- nonhemagglutinin --, therefor.

Signed and Sealed this
Twelfth Day of April, 2011

David J. Kappos
*Director of the United States Patent and Trademark Office*

CERTIFICATE OF CORRECTION (continued)
U.S. Pat. No. 7,811,586 B2

In column 6, line 50, delete "(NT201)" and insert -- (NT 201) --, therefor.

In column 8, line 1, delete "$A_{260}/A_{278}$of" and insert -- $A_{260}/A_{278}$ of --, therefor.

In column 9, line 35, after "palmar hyperhidrosis" delete "and other hyperhidrosis".

In column 10, line 32, delete "rhinittis," and insert -- rhinitis, --, therefor.

In column 10, line 58, delete "Nauny" and insert -- Naunyn --, therefor.

In column 10, line 62, delete "Nauny" and insert -- Naunyn --, therefor.

In column 11, line 28, delete "sphincters) )," and insert -- sphincters), --, therefor.

In column 11, line 40, delete "Toxin" and insert -- toxin --, therefor.

In column 12, line 3, delete "neurotransmifters" and insert -- neurotransmitters --, therefor.

In column 13, line 67, delete "epidimymitis." and insert -- epididymitis. --, therefor.

In column 16, line 5, delete "(epidimymitis)." and insert -- (epididymitis). --, therefor.

In column 16, line 42-55, delete "In some embodiments, a neurotoxin, such as a botulinum toxin type A or other types, can be locally administered according to the present disclosed methods in amounts of between about $10^{-3}$ U/kg to about 10 U/kg. In some embodiments, a neurotoxin, such as a botulinum toxin type A or other types, can be locally administered according to the present disclosed methods in amounts of between about $10^{-2}$ U/kg and about 1 U/kg. In some embodiments, a neurotoxin, such as a botulinum toxin type A or other types, can be locally administered according to the present disclosed methods in amounts of between about $10^{-1}$ U/kg and about 1 U/kg. Significantly, the pain alleviating effect of the present disclosed methods can persist for between about 2 months to about 6 months." and insert the same on Col. 16, Line 43, below "units." as a new paragraph.

In column 19, line 16, delete "ilioinginal" and insert -- ilioinguinal --, therefor.

In column 21, line 12, in claim 12, delete "A$_l$" and insert -- $A_1$ --, therefor.

In column 21, line 18, in claim 15, delete "epidimymitis." and insert -- epididymitis. --, therefor.

In column 22, line 17, in claim 23, delete "A$_l$" and insert -- $A_1$ --, therefor.